United States Patent
Fu et al.

(10) Patent No.: US 7,601,852 B2
(45) Date of Patent: Oct. 13, 2009

(54) MACROCYCLIC KINASE INHIBITORS

(75) Inventors: Hong Fu, Union City, CA (US); Yue Chen, Hayward, CA (US); Daniel V. Santi, San Francisco, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 110 days.

(21) Appl. No.: 11/729,327

(22) Filed: Mar. 27, 2007

(65) Prior Publication Data

US 2007/0265333 A1 Nov. 15, 2007

Related U.S. Application Data

(60) Provisional application No. 60/799,786, filed on May 11, 2006, provisional application No. 60/817,260, filed on Jun. 28, 2006.

(51) Int. Cl.
*C07D 313/00* (2006.01)
(52) U.S. Cl. .......................... 549/266; 549/267
(58) Field of Classification Search ................. 549/266, 549/267
See application file for complete search history.

(56) References Cited

U.S. PATENT DOCUMENTS

| | | | |
|---|---|---|---|
| 5,795,910 | A | 8/1998 | Giese |
| 6,635,671 | B1 | 10/2003 | Kastelic et al. |
| 2004/0224936 | A1 | 11/2004 | Chiba |
| 2005/0182129 | A1 | 8/2005 | Ikeda |
| 2005/0256183 | A1 | 11/2005 | Kasibhatla |
| 2006/0079494 | A1 | 4/2006 | Santi |
| 2006/0094674 | A1 | 5/2006 | Neel |

FOREIGN PATENT DOCUMENTS

| | | | |
|---|---|---|---|
| EP | 0606044 A1 | | 7/1994 |
| GB | 2323845 | * | 10/1998 |
| GB | 2323845 A1 | | 10/1998 |
| JP | 08-040893 | | 2/1996 |
| JP | 2001-294527 | | 10/2001 |
| WO | WO 02/48135 A1 | | 6/2002 |
| WO | WO 02/48136 A1 | | 6/2002 |

OTHER PUBLICATIONS

Patani et al. Chem.Rev. 1996, 96, 3147-3176.*
Horn et al. J. Med. Chem. 1984,27, 1340-1343.*
Davies et al., *Nature* 2002, 417, 949-954, "Mutations of the BRAF Gene in Human Cancer".
Dombrowski et al., *J. Antibiotics* 1999, 52 (12), 1077-1085, "Production of a Family of Kinase-Inhibiting Lactones from Fungal Fermentations".
Ellestad et al., *J. Org. Chem.* 1980, 43 (12), 2339-2343, "New Zearalenone Related Macrolides and Isocoumarins from an Unidentified Fungus".
Nair et al., *Tetrahedron Letters* 1980, 21 (21), 2011-2012, "Metabolites of pyrenomycetes. XIII. Structure of (+)-hypothemycin, an antibiotic macrolide from *Hypomyces trichothecoides*" (abstract).
Sausville et al., *Ann. Rev. Pharmacol. Toxicol.* 2003, 43, 199-231, "Signal Transduction-Directed Cancer Treatments".
Selles et al., *Tetrahedron Letters* 2002, 43 (26), 4627-4631, "Convergent stereospecific synthesis of LL-Z1640-2 (or C292), hypothemycin and related macrolides. Part 2".
Tatsuta et al., *Chemistry Letters* 2001, 2, 172-173, "The First Total Synthesis of a Macrocyclic Antiprotozoan, LI-Z1640-2".
Wermuth, ed., *The Practice of Medicinal Chemistry*, 2nd Ed., pp. 561-586 (Academic Press 2003).
Williams et al., *Biochemistry* 1998, 37, 9579-9585, "Ro 09-2210 Exhibits Potent Antiproliferative Effects on Activated T Cells by Selectively Blocking MKK Activity".
Patani et al., Bioisosterism: A Rational Approach in Drug Design, Chem. Rev., vol. 96, pp. 3147-3176 (1996).

* cited by examiner

*Primary Examiner*—D. Margaret Seaman
*Assistant Examiner*—Nizal S Chandrakumar
(74) *Attorney, Agent, or Firm*—Elliott Korsen

(57) ABSTRACT

A compound having a structure according to formula I

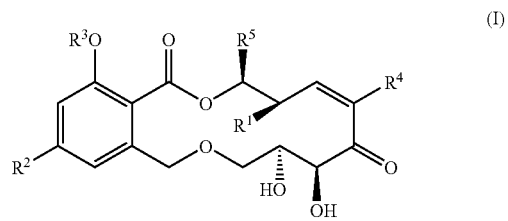

wherein $R^1$, $R^2$, $R^3$, $R^4$, and $R^5$ are as defined herein, are useful as kinase inhibitors.

6 Claims, 7 Drawing Sheets

$^1$H NMR Spectrum of Compound 29

13C NMR Spectrum of Compound 29

¹H NMR Spectrum of Compound 30

13C NMR Spectrum of Compound 30

MACROCYCLIC KINASE INHIBITORS

CROSS-REFERENCE TO RELATED APPLICATIONS

This application claims the benefit under 35 U.S.C. §119(e) of U.S. Provisional Applications Nos. 60/799,786, filed May 11, 2006, and 60/817,260, filed Jun. 28, 2006, the disclosures of which are incorporated herein by reference.

BACKGROUND OF THE INVENTION

1. Field of the Invention

This invention relates to compounds useful as kinase inhibitors and methods for their preparation and use.

2. Description of Related Art

Protein kinases ("kinases") constitute a large family of enzymes that phosphorylate other proteins with adenosine triphosphate ("ATP") as the phosphate source. They include serine kinases and tyrosine kinases, which phosphorylate hydroxyl groups on serine and tyrosine residues, respectively, on their target proteins. Kinases can also be dual function, meaning that they phosphorylate both serine and tyrosine residues. The target protein can be an enzyme, a membrane channel, or other protein.

Cellular activity is often controlled by an external signaling molecule (e.g., a hormone or a mitogen), whose binding to a cognate receptor at the cell surface stimulates or inhibits various intracellular events. The initial signaling molecule-receptor interaction triggers a signaling cascade, or cell-signaling pathway, of additional protein interactions within the cell, often involving the kinase-mediated phosphorylation of proteins (signal transduction). Thus, at the molecular level, cellular activities are regulated by the phosphorylation (and dephosphorylation) of associated kinases and other proteins such as transcription factors. Cellular activities so regulated include cell growth, cell division, and apoptosis.

Many diseases of unwanted cell proliferation (such as cancer, psoriasis, restenosis) are characterized by disruptions in a signaling cascade, causing cell proliferation to become unchecked. Often, the disruption arises from a single mutation in a protein located upstream in the signal cascade, affecting the regulation of multiple kinases downstream. Thus, inhibition of the affected kinase(s) has been advanced as a basis for the treatment of cancer. Sausville et al., *Ann. Rev. Pharmacol. Toxicol.* 2003, 43, 199-231, "Signal Transduction-Directed Cancer Treatments".

The resorcylic acid lactones ("RALs") are a family of natural products having a 14-member lactone ring incorporating a resorcylic acid residue, an example being hypothemycin:

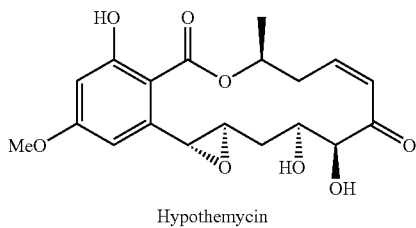

Hypothemycin

There exist several disclosures that RALs—and their semi-synthetic or synthetic analogs or derivatives—are kinase inhibitors and therefore are useful for treating diseases characterized by abnormal kinase activity. See, e.g., Giese et al., U.S. Pat. No. 5,795,910 (1998); Chiba et al., US 2004/0224493 A1 (2004); and Santi et al., US 2006/0079494 A1 (2006).

The present invention provides novel compounds—which may be viewed as RAL analogs—that are effective kinase inhibitors and are useful for treating a disease or condition amenable to treatment by inhibition of a kinase.

BRIEF SUMMARY OF THE INVENTION

In one embodiment, this invention provides a compound having a structure represented by formula I

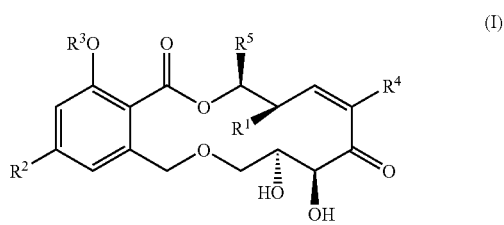

(I)

and the pharmaceutically acceptable esters, salts, solvates, and hydrates thereof, wherein $R^1$ is H, $C_1$-$C_4$ alkyl, $C_2$-$C_4$ alkenyl, or $C_2$-$C_4$ alkynyl;

$R^2$ is H, halogen, hydroxyl, protected hydroxyl, $OR^{12}$, $SR^{12}$, $NR^{12}R^{13}$, —$X^1(CH_2)_pX^2$—$R^{14}$, or is alkyl optionally substituted with hydroxyl, protected hydroxyl, halogen, amino, protected amino, or —$X^1(CH_2)_pX^2$—$R^{14}$;

wherein $R^{12}$ and $R^{13}$ are, independently for each occurrence thereof, H or an optionally substituted aliphatic, optionally substituted cycloaliphatic, optionally substituted heterocycloaliphatic, optionally substituted aryl, or optionally substituted heteroaryl moiety or an N or S protecting group, or $R^{12}$ and $R^{13}$, taken together form a saturated or unsaturated cyclic ring containing 1 to 4 carbon atoms and 1 to 3 nitrogen or oxygen atoms; each of $R^{12}$ and $R^{13}$ being optionally substituted with one or more occurrences of hydroxyl, protected hydroxyl, alkoxy, amino, protected amino, —NH(alkyl), aminoalkyl, or halogen;

$X^1$ and $X^2$ are each independently absent, oxygen, NH, or —N(alkyl), or wherein $X^2$—$R^{14}$ together are $N_3$ or are a heterocycloaliphatic moiety;

p is an integer from 1 to 10, inclusive, provided that p can be 1 only when at least one of $X^1$ and $X^2$ is absent; and $R^{14}$ is H or an aryl, heteroaryl, alkylaryl, or alkylheteroaryl moiety, or is —(C=O)NHR$^{15}$, —(C=O)OR$^{15}$, or —(C=O)R$^{15}$, wherein each occurrence of $R^{15}$ is independently H or an aliphatic, cycloaliphatic, heterocycloaliphatic, aryl, or heteroaryl moiety; or $R^{14}$ is —$SO_2$($R^{16}$), wherein $R^{16}$ is an aliphatic moiety; wherein one or more of $R^{14}$, $R^{15}$, and $R^{16}$ is optionally substituted with one or more occurrences of hydroxyl, protected hydroxyl, alkoxy, amino, protected amino, —NH(alkyl), aminoalkyl, or halogen;

$R^3$ is H, a hydroxyl protecting group, $C_1$-$C_4$ alkyl, $C_2$-$C_4$ alkenyl, $C_2$-$C_4$ alkynyl, $CO(C_1$-$C_4$ alkyl), $CO(C_2$-$C_4$ alkenyl), or $CO(C_2$-$C_4$ alkynyl);

$R^4$ is H or halogen; and $R^5$ is H, $C_1$-$C_4$ alkyl, $C_2$-$C_4$ alkenyl, or $C_2$-$C_4$ alkynyl, or $R^1$ and $R^5$ combine to form $(CH_2)_n$, where n is 1, 2, 3, or 4.

In another embodiment, this invention provides a method for treating a subject suffering from a disease characterized by the proliferation of cells having abnormally elevated activity of at least one kinase, comprising administering to the subject a therapeutically effective amount of a compound of this invention. Preferably, the disease so treated is melanoma, colon cancer, or breast cancer, especially melanoma or colon cancer.

In another embodiment, this invention provides a method for inhibiting the proliferation of a cell having by abnormally elevated activity of at least one kinase, comprising contacting the cell with a compound of this invention.

In another embodiment, this invention provides a method for inhibiting a kinase having an active site cysteine residue, comprising contacting the kinase with a compound according to this invention.

In another embodiment, this invention provides the use of a compound of this invention for the preparation of a medicament for the treatment of a disease characterized by the proliferation of cells having abnormally elevated activity of at least one kinase.

BRIEF DESCRIPTION OF THE DRAWING(S)

FIGS. 1, 2, 3a, and 3b show schemes for making intermediates utilized in the synthesis of compounds of this invention.

DETAILED DESCRIPTION OF THE INVENTION

Definitions

Figure 1:
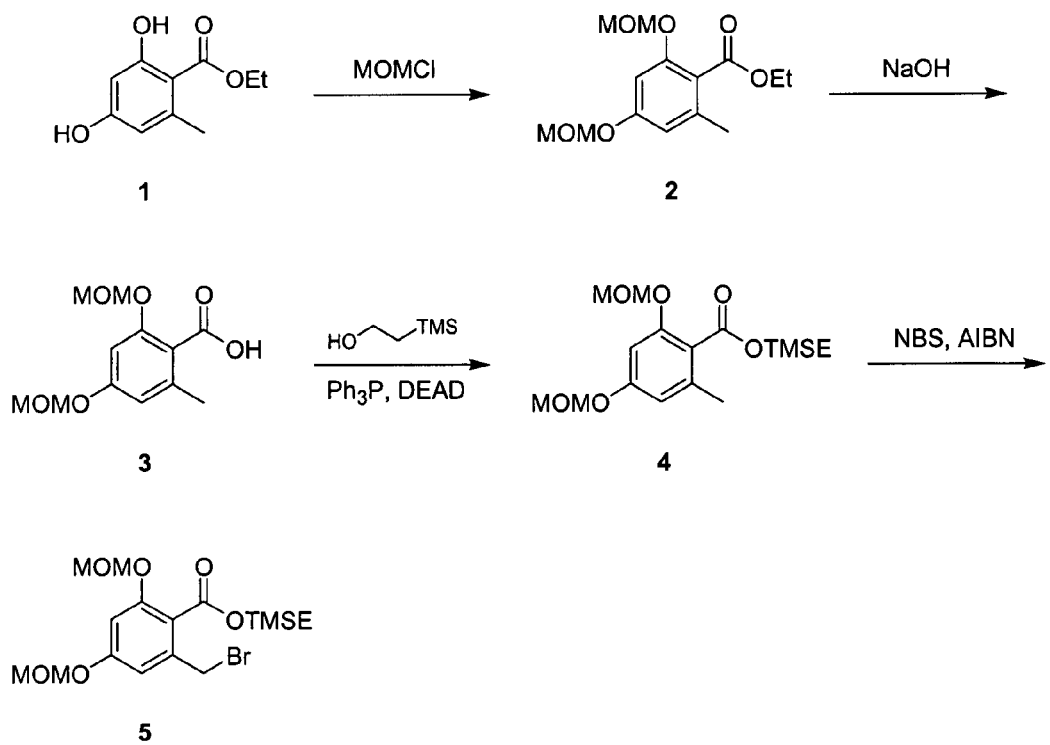

"Aliphatic" means a straight- or branched-chain, saturated or unsaturated, non-aromatic hydrocarbon moiety having the specified number of carbon atoms (e.g., as in "$C_3$ aliphatic," "$C_1$-$C_5$ aliphatic," or "$C_1$ to $C_5$ aliphatic," the latter two phrases being synonymous for an aliphatic moiety having from 1 to 5 carbon atoms) or, where the number of carbon atoms is not specified, from 1 to 4 carbon atoms (2 to 4 carbons in the instance of unsaturated aliphatic moieties).

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-phenyl), cis-1-propenyl, trans-1-propenyl, E- (or Z-)-2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings and each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like.

"Alkoxy", "aryloxy", "alkylthio", and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like.

Where it is indicated that a moiety may be substituted, such as by use of "substituted or unsubstituted" or "optionally substituted" phrasing as in "substituted or unsubstituted $C_1$-$C_5$ alkyl" or "optionally substituted heteroaryl," such moiety may have one or more independently selected substitutents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl", (heterocycloaliphatic)alkyl", "arylalkenyl", "arylalkynyl", "biarylalkyl", and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl", "alkenylcycloalkyl", and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl", "haloalkyl", "alkylaryl", "cyanoaryl", and the like mean an alkyl, aryl, etc., moiety, as the case may be, substituted with one or more of the identified substituent (hydroxyl, halo, etc., as the case may be).

By way of illustration, permissible substituents include, but are not limited to, is alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO (alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O) (alkyl), —NHC(=O)H, —NHC(=O)NH$_2$, —NHC(=O)NH(alkyl), —NHC(=O)N(alkyl)$_2$, and —NHC(=NH)NH$_2$.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(cycloalkyl), —O(heterocycloalkyl), —O(aryl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$.

A protecting group, as in "protected hydroxyl" or "hydroxyl protecting group," is a group that can be selectively attached to a hydroxyl group on a compound to render the hydroxyl group inert to certain chemical reaction conditions to which the compound is exposed and that, after such exposure, can be selectively removed. Many examples of hydroxyl protecting groups are known. See, for instance, Greene and Wuts, *Protective Groups in Organic Synthesis,* 3rd edition, pp. 17-245 (John Wiley & Sons, New York, 1999), the disclosure of which is incorporated herein by reference. Exemplary suitable hydroxyl protecting groups include for use with compounds of this invention include t-butyldimethylsilyl ("TBDMS" or "TBS"), triethylsilyl ("TES") and triphenylsilyl ("TPS").

Where a range is stated, as in "$C_1$ to $C_5$ alkyl" or "5 to 10%," such range includes the end points or boundaries of the range.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention.

"Pharmaceutically acceptable salt" means a salt of a compound suitable for pharmaceutical formulation. Where a compound has one or more basic functionalities, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic moieties, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

"Therapeutically effective amount" means that amount of active compound(s) or pharmaceutical agent(s) that elicit the biological or medicinal response in a tissue system, animal or human sought by a researcher, veterinarian, medical doctor or other clinician, which response includes alleviation of the symptoms of the disease or disorder being treated. The specific amount of active compound(s) or pharmaceutical agent(s) needed to elicit the biological or medicinal response will depend on a number of factors, including but not limited to the disease or disorder being treated, the active compound(s) or pharmaceutical agent(s) being administered, the method of administration, and the condition of the patient.

Compounds and Methods

In a preferred embodiment of compounds having a structure represented by formula I, $R^1$ is H or $C_1$-$C_4$ alkyl (most preferably H or Me); $R^2$ is OH, protected hydroxyl, O($C_1$-$C_4$ alkyl), O($C_2$-$C_4$ alkenyl), O($C_2$-$C_4$ alkynyl), OC(=O)($C_1$-$C_4$ alkyl), OC(=O)($C_2$-$C_4$ alkenyl), or OC(=O)($C_2$-$C_4$ alkynyl); $R^3$ is H, a hydroxyl protecting group, $C_1$-$C_4$ alkyl, $C_2$-$C_4$ alkenyl, $C_2$-$C_4$ alkynyl, CO($C_1$-$C_4$ alkyl), CO($C_2$-$C_4$ alkenyl), or CO($C_2$-$C_4$ alkynyl); $R^4$ is H; and $R^5$ is Me.

In another preferred embodiment, $R^3$ and $R^4$ are both H and $R^5$ is Me, corresponding to a compound having a structure represented by formula (II)

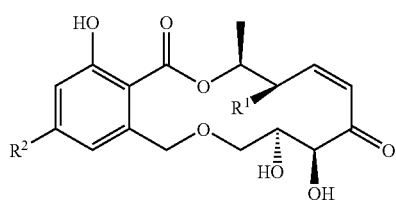

(II)

wherein $R^1$ and $R^4$ have the meanings assigned in the BRIEF SUMMARY OF THE INVENTION section hereinabove. More preferably $R^1$ is H or $C_1$-$C_4$ alkyl and $R^2$ is OH, protected hydroxyl, O($C_1$-$C_4$ alkyl), O($C_2$-$C_4$ alkenyl), O($C_2$-$C_4$ alkynyl), OC(=O)($C_1$-$C_4$ alkyl), OC(=O)($C_2$-$C_4$ alkenyl), or OC(=O)($C_2$-$C_4$ alkynyl). Even more preferably, $R^1$ is H or Me and $R^2$ is OH, O($C_1$-$C_4$ alkyl), or OC(=O)($C_1$-$C_4$ alkyl).

Figure 4:
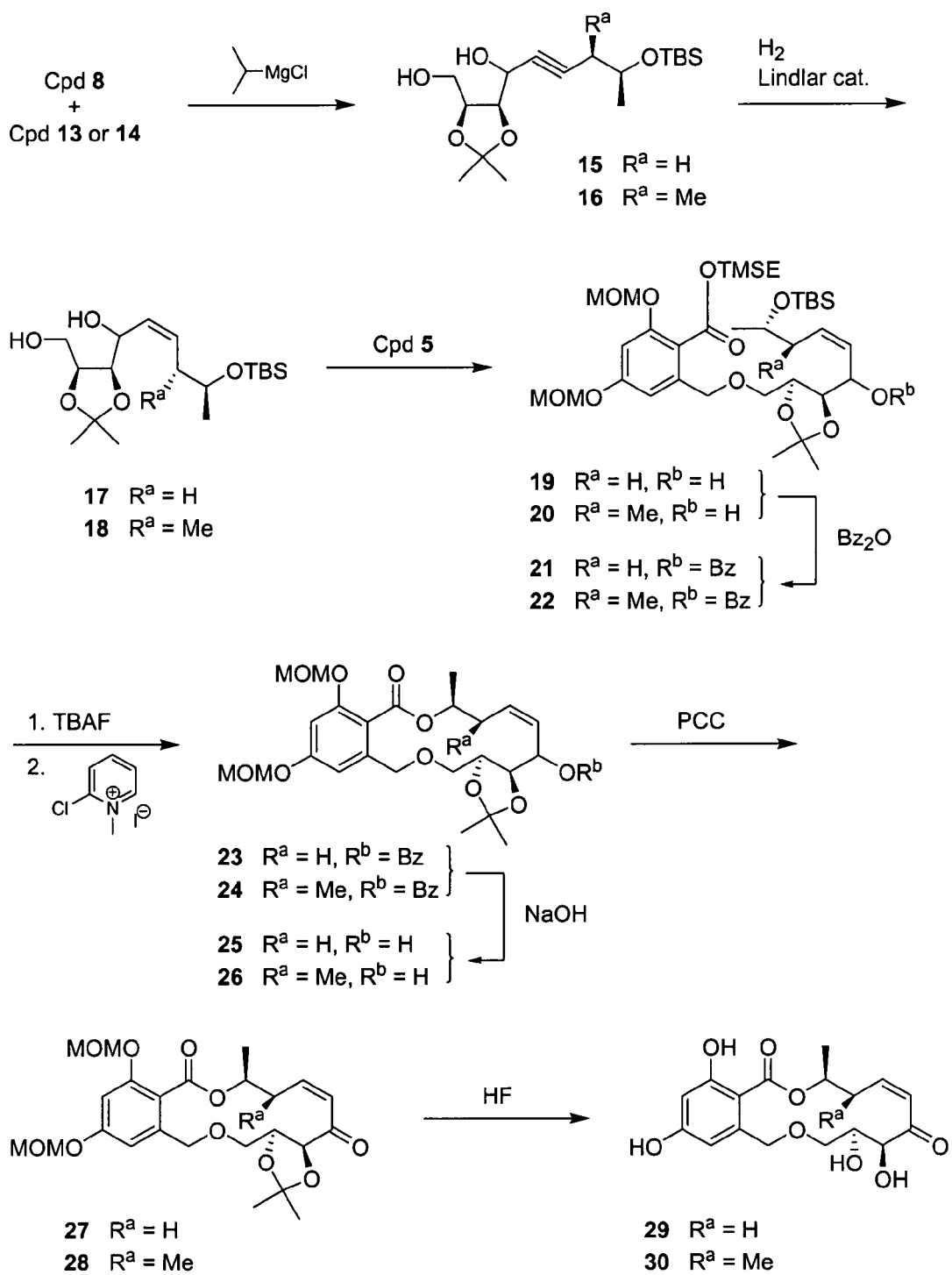
FIG. 4 shows a scheme for making compounds of this invention, utilizing intermediates made per FIGS. 1 through 3.

Specific compounds of this invention have structures represented formulae by III and IV (also depicted as compounds 29 and 30, respectively, in FIG. 4).

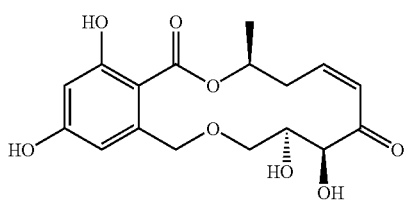

(III)

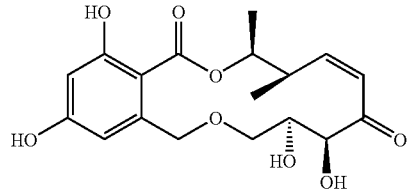

(IV)

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described herein with a compound within the parameters of formula I or with a compound not within such parameters, but which converts to the specified compound in vivo after administration to a subject in need thereof. Conventional procedures for the selection and preparation of suitable prodrug derivatives are described, for example, in Wermuth, "Designing Prodrugs and Bioprecursors," in Wermuth, ed., *The Practice of Medicinal Chemistry*, 2nd Ed., pp. 561-586 (Academic Press 2003), the disclosure of which is incorporated herein by reference. Prodrugs include esters that hydrolyze in vivo (for example in the human body) to produce a compound of this invention or a salt thereof. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include but are not limited to formates, acetates, propionates, butyrates, acrylates, citrates, succinates, and ethylsuccinates, attached to one or more of the phenolic oxygens or either one or more of the aliphatic OH groups.

The abnormally elevated kinase activity that can be targeted by compounds of this invention can arise in a number of ways. The kinase can be present in a normal amount but upstream disruptions in the signaling pathway have left its activity unregulated. Or, the kinase can be present in an abnormally elevated amount. Or, the kinase can be mutated, so that it is active but unresponsive to regulatory signals.

Santi et al., US 2006/0079494 A1 (2006), have proposed that hypothemycin and other RAL analogs having a cis-enone moiety are covalent inhibitors of kinases whose active site contains a cysteine residue located between, and immediately adjacent to one of, two aspartate residues in the ATP-binding site of the kinase. (The aspartate residues interact with a phosphate group in and also with the $Mg^{+2}$ ion complexed with the phosphate groups of the ATP and represent a highly conserved motif in kinases.) They postulated that the cysteine sulfhydryl group adds across the enone double bond in a Michael reaction, forming a covalent adduct that is irreversible or only very slowly reversible (illustrated below using hypothemycin as a representative RAL):

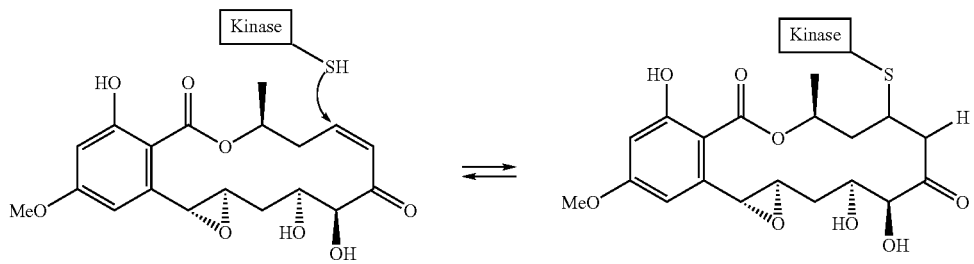

They screened hypothemycin against a panel of 124 kinases, of which 19 had such an active site cysteine and the rest did not. Hypothemycin inhibited 20 kinases, 18 of which had the active site cysteine. That is, hypothemycin inhibited 18 of the 19 active site cysteine kinases, but only 2 of 105 kinases not having such an active site cysteine, providing empirical support for the Michael reaction hypothesis.

Without being bound by theory, it is believed that compounds of this invention can act by a similar mechanism to kinases. Thus, in one preferred embodiment, a kinase inhibited by a compound of this invention has a cysteine residue located between, and immediately adjacent to one of, two aspartate residues in the ATP-binding site of the kinase.

In another preferred embodiment, the active-site cysteine kinase that is inhibited by compounds of this invention is selected from the group consisting of AAK1, APEG1 splice variant with kinase domain (SPEG), BMP2K (BIKE), CDKL1, CDKL2, CDKL3, CDKL4, CDKL5 (STK9), ERK1 (MAPK3), ERK2 (MAPK1), FLT3, GAK, GSK3A, GSK3B, KIT (cKIT), MAP3K14 (NIK), MAP3K7 (TAK1), MAPK15 (ERK8), MAPKAPK5 (PRAK), MEK1 (MKK1, MAP2K1), MEK2 (MKK2, MAP2K2), MEK3 (MKK3, MAP2K3), MEK4 (MKK4, MAP2K4), MEK5 (MKK5, MAP2K5), MEK6 (MKK6, MAP2K6), MEK7 (MKK7, MAP2K7), MKNK1 (MNK1), MKNK2 (MNK2, GPRK7), NLK, PDGFR alpha, PDGFR beta, PRKD1 (PRKCM), PRKD2, PRKD3 (PRKCN), PRPF4B (PRP4K), RPS6KA1 (RSK1, MAPKAPK1A), RPS6KA2 (RSK3, MAPKAP1B), RPS6KA3 (RSK2, MAPKAP1C), RPS6KA6 (RSK4), STK36 (FUSED_STK), STYK1, TGFBR2, TOPK, VEGFR1 (FLT1), VEGFR2 (KDR), VEGFR3 (FLT4) and ZAK. These kinases are believed to have the two-aspartate/cysteine active motif discussed hereinabove.

B-Raf is a kinase in the Ras-Raf-MEK1/2-ERK1/2-MAP cell signaling pathway. Mutated B-Raf is found in about 70% of malignant melanomas and 20% of colon cancers and has also been found in breast cancer. Commonly, the B-Raf mutation is a single substitution designated as V600E (V599E in older literature), where a valine is replaced by glutamic acid at amino acid position 600 (599 in older literature). Davies et al., Nature 2002, 417, 949-954, "Mutations of the BRAF Gene in Human Cancer." This single mutation is oncogenic: it constitutively activates the signaling pathway, so that the activity of the downstream kinases MEK1/2 and ERK1/2—and cell proliferation—is unchecked. However, ERK1, ERK2, MEK1, and MEK2 are susceptible to inhibition by compounds of this invention as kinases having the requisite active site cysteine. Thus, in one preferred embodiment, compounds of this invention are used to inhibit the proliferation of cells characterized by having a B-Raf V600E mutation. In this manner, a single compound can inhibit plural target molecules associated with a disease condition.

In another embodiment, compounds of this invention are useful for treating a disease characterized by the proliferation of cells having mutated B-Raf. Preferably, before treatment, the subject is screened for the presence of a B-Raf mutation (especially a V600E mutation) in the proliferating cells and hence, the subject's likelihood of responding positively to treatment.

Typically, the inventive compound will be part of a pharmaceutical composition or preparation that may be in any suitable form such as solid, semisolid, or liquid form. In general, the pharmaceutical preparation will contain one or more of the compounds of the invention as an active ingredient and a pharmaceutically acceptable carrier or excipient. Typically the active ingredient is in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use.

Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

The amount of active ingredient that can be combined with the carrier materials to produce a single dosage form will vary depending upon the host treated and the particular mode of administration. For example, a formulation intended for oral administration to humans can contain carrier material, which can vary from about 5 percent to about 95 percent of the total composition. Dosage unit forms will generally contain from about 5 mg to about 500 mg of active ingredient.

A therapeutically effective amount of compounds of this invention can be administered to a subject in a single or in divided doses. The frequency of administration can be daily, or according some other regular schedule (e.g., every 3rd day), or even according to an irregular schedule. The dosage can be in amounts, for example, of from about 0.01 to about 10 mg/kg body weight, or more usually, from about 0.1 to about 2 mg/kg body weight.

It will be understood, however, that the specific dose level for any particular patient may depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

The subject is typically a human, although the methods of the invention can be practiced for veterinary purposes, with suitable adjustment of the unit dose for another mammal of interest (including cats, cattle, dogs, horses, and the like).

The practice of this invention can be further understood by reference to the following examples, which are provided by way of illustration and not of limitation.

EXAMPLE 1

Benzylic Bromide 5

This example describes the synthesis of benzylic bromide 5, which is an intermediate in the synthesis of compounds of this invention such as compounds 29 and 30. The synthetic scheme is summarized in FIG. 1. The $^1$H NMR spectra of the products obtained were in each instance consistent with the assigned structures.

MOM-protected ester 2. To a solution of ethyl 2,4-dihydroxy-6-methylbenzoate 1 (15 g, 76.45 mmol) in dry dichloromethane ("DCM", 75 mL) was added 1,8-diazabicyclo[5.4.0]undec-7-ene ("DBU", 45.7 mL, 305.8 mmol) at 0° C. The solution turned brown. Chloromethyl methyl ether ("MOMCl", 14.5 mL, 191.1 mmol) was added drop-wise at 0° C. The reaction was stirred at room temperature ("RT") for 12 hours. DBU (22.3 mL, 153 mmol) and MOMCl (7.25 mL, 95.6 mmol) were added and the reaction was stirred at 35° C. for 2 hours. Diethyl ether (200 mL) and water (100 mL) were added and the layers were separated. The aqueous layer was extracted with diethyl ether (3×100 mL). The combined organic layers were washed with water (100 mL), 5% NaHSO$_4$ (50 mL), water (50 mL), sat. NaHCO$_3$ (50 mL), and brine (50 mL), dried over Na$_2$SO$_4$, filtered through a pad of silica gel and MgSO$_4$, and evaporated to dryness. MOM-protected ester 2 (19.5 g) was obtained after drying under high vacuum.

MOM-protected acid 3. To a solution of MOM-protected ester 2 (5.12 g, 18 mmol) in water (20 mL) and MeOH (20 mL) was added NaOH (2.88 g). The reaction mixture was heated at 83° C. for 18 h. The MeOH was removed and ethyl acetate ("EtOAc", 50 mL) was added. The pH of the aqueous phase was adjusted to pH 2-3 with NaHSO$_4$ (~9 g in 20 mL water). The aqueous layer was extracted with EtOAc (3×50 mL) and the combined organic layers were washed with brine (50 mL), dried over Na$_2$SO$_4$, filtered through a pad of silica gel and MgSO$_4$, and evaporated to dryness. The crude MOM-protected acid 3 was azeotroped with toluene (2×) and used for next step without purification.

TMSE ester 4. To a solution of MOM-protected acid 3 (~18 mmol), triphenylphosphine ("Ph$_3$P", 6.14 g, 23.4 mmol), and trimethylsilylethanol ("TMSE-OH", 3.08 mL, 21.6 mmol) in ether (40 mL) and toluene (12 mL) was added diethyl azodicarboxylate ("DEAD", 10.2 g, 40% in toluene) at 0° C. drop-wise. The reaction mixture was stirred at RT for 12 h. Hexanes were added and the solid was filtered off. The mother liquid was concentrated and filtered again and washed with more hexanes. The solvent was removed and TMSE ester 4 (5.06 g) was purified by silica gel column (10-20% EtOAc in hexane).

Benzylic bromide 5. To a solution of TMSE ester 4 (10.16 g, 28.03 mmol) in CCl$_4$ (300 mL) was added azaisobutyronitirle ("AIBN", 0.46 g, 2.8 mmol) and N-bromosuccinimide ("NBS", 5.49 g, 30.83 mmol). The resulting suspension was degassed four times (with nitrogen flushing) and irradiated with strong light (3 sun lamps, total 1000 w). The stirred suspension was heated to reflux rapidly and stirred for 1 hour to yield a light yellow solution (reaction progress monitored by NMR). After cooling to RT, the reaction mixture washed with saturated NaHCO$_3$ (3×30 mL), H$_2$O (30 mL) and brine (30 mL). The organic solution was dried over anhydrous NaSO$_4$, filtered through a pad of silica gel and concentrated. The residue was purified by column chromatography (EtOAc in hexanes, 0% to 24% gradient) to give benzylic bromide 5 as a colorless oil (8.5 g, 65-70% pure; contaminated with ~20% starting material and ~10% phenyl brominated product).

EXAMPLE 2

Tetrahydrofuran-2-ol 8

Figure 2:
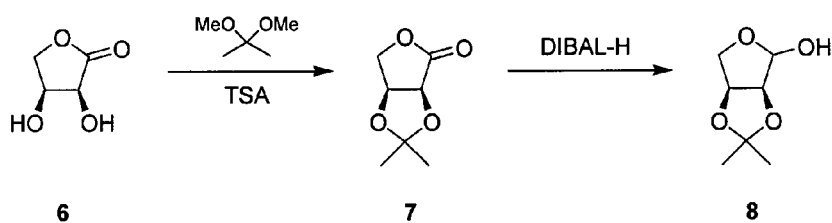

This example describes the synthesis of tetrahydrofuran-2-ol 8, which also is an intermediate in the synthesis of compounds of this invention such as compounds 29 and 30. The synthetic scheme is summarized in FIG. 2. The $^1$H NMR spectra of the products obtained were in each instance consistent with the assigned structures.

Ketal lactone 7. 2,2-Dimethoxypropane (126 mL) and p-toluenesulfonic acid ("TSA", 633 mg) were added to a solution of L-erythrono-1,4-lactone 6 (15 g) in N,N-dimethylformamide ("DMF", 158 mL). The mixture was refluxed under N$_2$ for 2 hours and then kept at RT over night. DCM (500 mL) was added and the organic phase washed with saturated NaHCO$_3$ (5×300 mL), dried over Na$_2$SO$_4$, filtered, and evaporated to dryness. Ketal lactone 7 (9.8 g) was obtained after silica gel column chromatography (10%-50% ethyl acetate in hexane).

Tetrahydrofuran-2-ol 8. Diisobutylaluminum hydride ("DIBAL-H", 1 eq, neat) was added dropwise to a solution of ketal lactone 7 (9.8 g) in DCM (100 mL) at −78° C. The reaction was stirred at −78° C. for 1 h and quenched with saturated NH$_4$Cl. EtOAc (500 mL) was added and the organic phase washed with saturated NH$_4$Cl (2×300 mL), washed with brine (2×300 mL), dried over Na$_2$SO$_4$, filtered, and evaporated to dryness. Tetrahydrofuran-2-ol 8 (7.5 g) was obtained after silica gel column chromatography (DCM to 5% MeOH in DCM).

EXAMPLE 3

Acetylenic TBS Ethers 13 and 14

This example describes the synthesis of acetylenic TBS ethers 13 and 14, which are intermediates in the synthesis of compounds of this invention such as compounds 29 and 30, respectively. The $^1$H NMR spectra of the products obtained were in each instance consistent with the assigned structures.

Figure 3A:
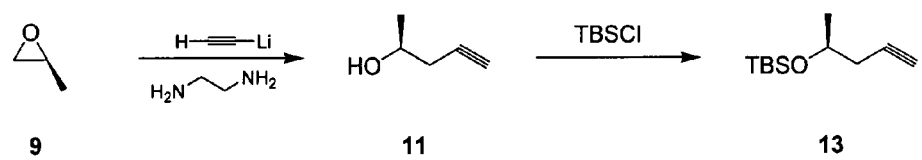

The synthetic scheme for TBS ether 13 is summarized in FIG. 3a.

Acetylenic alcohol 11. Lithium acetylene-ethylene diamine complex (24.92 g, 0.271 mol) in dimethylsulfoxide (DMSO, 250 mL) was added dropwise at 4° C. to (S)-propylene oxide 9 (17.3 mL, 0.246 mol). The reaction mixture was stirred at RT for 24 h, poured into ice water, and extracted with ether (4×360 mL). The combined organic layers were washed with saturated NH$_4$Cl, dried over Na$_2$SO$_4$, filtered, and evaporated to dryness. Crude acetylenic alcohol 11 (39 g) was obtained and used for next step without purification.

Acetylenic TBS ether 13. Imidazole (16.7 g, 0.246 mol) and tributyl silyl chloride ("TBSCl", 25 g, 0.166 mol) in 10 portions were added to the crude acetylenic alcohol 11 (39 g, 0.123 mol) in DCM (250 mL) at RT. The reaction mixture was stirred at RT for 3 h. Hexanes (600 mL) and saturated aqueous NaHCO$_3$ (300 mL) were added and the layers were separated.

The organic layers were washed with water (3×400 mL), dried over Na$_2$SO$_4$, filtered, and evaporated to dryness. Crude acetylenic TBS ether 13 (19 g) was obtained after silica gel column chromatography (100% hexanes).

Figure 3B:
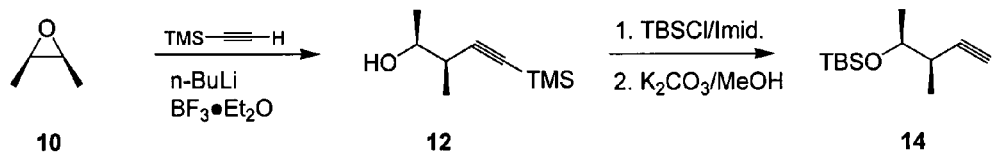

The synthetic scheme for TBS ether 14 is summarized in FIG. 3b. Generally, the procedure of Chiba et al., US 2004/0224936 A1 (2004) was followed. Two enantiomers were obtained and used for the next step.

Acetylenic alcohol 12. n-BuLi (110 mL, 2.5 M) was added to a solution of TMS-acetylene (38.8 mL) in 1 L THF at −60° C. The reaction was warmed to 0° C. briefly, then cooled back down to −60° C. BF$_3$.Et$_2$O (33.8 mL) was then added slowly, followed by the epoxide 10 (15 mL) via syringe pump over 2 hours. After stirring at −60° C. for 1.5 hours, the reaction mixture was warmed to room temperature, quenched with saturated NH$_4$Cl (500 mL), and extracted with ethyl acetate (2×2 L). The organic layers were combined, dried, and concentrated. The crude product was purified by silica gel column chromatography with 4:1 hexanes/EtOAc to give 13.9 g of desired acetylenic alcohol 12 as an oil.

Acetylenic TBS ether 14. To alcohol 12 in 280 mL dichloromethane at room temperature, was added imidazole (19.2 g). TBSCl (32 g) was added in five portions. The reaction mixture was stirred at room temperature for 3 hours. Hexane (700 mL) was added and the organic layer wash with brine (350 mL) then water (3×450 mL), dried over Na$_2$SO$_4$, filtered, and evaporated to dryness. The product was purified by silica gel column chromatography (hexanes) to give 8.7 g intermediate TBS protected TMS acetylene.

A mixture of the TBS protected TMS acetylene (8.7 g) and K$_2$CO$_3$ (8 g) in methanol (120 mL) was stirred for 5 hours at room temperature. The mixture was extracted with ethyl acetate (2×200 mL). The combined organic layers were dried and concentrated. The crude product was purified on silica gel column with hexanes eluent to give 6.17 g of ether 14 as a colorless oil. Two enantiomers were obtained and used for the next step.

EXAMPLE 4

Compound 29

This example describes the synthesis of one of the compounds of this invention, namely compound 29. The synthetic scheme is shown in FIG. 4. The $^1$H NMR spectra of the products obtained were in each instance consistent with the assigned structures. Further, additional analytical data were obtained for compound 29.

Yne-diol 15. Isopropyl magnesium chloride (3.13 mL, 6.25 mmol, 2.0 M in tetrahydrofuran ("THF")) was added to a solution of acetylenic TBS ether 13 (1.24 g, 6.25 mmol) in THF (3.1 mL) at 0° C. The reaction mixture was heated to 50° C. and stirred at that temperature for 1 hour, cooled to 0° C. A solution of tetrahydrofuran-2-ol 8 in 5 mL THF was added. The reaction mixture was stirred at RT for 4 h, quenched by addition of saturated NaH$_2$PO$_4$ (20 mL). The aqueous layer was extracted with EtOAc (4×30 mL). The combined organic layers were dried over Na$_2$SO$_4$, filtered, and evaporated to dryness. Yne-diol 15 (2.33 g) was obtained as a single diastereomer after silica gel column chromatography (10%-40% EtOAc in hexane).

Ene-diol 17. Lindlar catalyst (210 mg) and quinoline (10 μL) were added to a solution of yne-diol 15 (789 mg) in hexanes (40 mL). The reaction mixture was degassed, filled with H$_2$ three times, and stirred under H$_2$ for 1 h. The reaction mixture was filtered through a pad of silica gel and concentrated. Ene-diol 17 (701 mg) was obtained after silica gel column chromatography (10%-40% EtOAc in hexane).

Alcohol 19. A solution of ene-diol 17 (2.47 g, 6.85 mmol) in dry THF (10 mL) was added slowly to a suspension of NaH (343 mg, 8.56 mmol, 60% in mineral oil, washed with hexanes) in THF (15 mL) at −30° C. The reaction mixture was stirred at RT for 2 h. After cooling to −30° C., a solution of benzyl bromide 5 in THF (6 mL) was added dropwise and the resulting reaction mixture was stirred at RT for 2 h. The reaction was stopped by addition of phosphate buffer (pH 7, 1.0M, 30 mL). Ethyl ether (100 mL) was added and the layers were separated. The aqueous layer was extracted with ether (2×30 mL). The combined organic layers were dried over Na$_2$SO$_4$, filtered, and evaporated to dryness. Alcohol 19 (824 mg, 80% pure) was obtained after silica gel column chromatography (5%-20% EtOAc in hexane).

Benzoate 21. To a solution of alcohol 19 (460 mg, 0.636 mmol) in dry DCM (5 mL), was added diisopropylethylamine (0.544 mL, 3.18 mmol), benzoic anhydride (288 mg, 1.27 mmol), and 4-dimethylaminopyridine ("DMAP", 71.3 mg, 0.636 mmol). The reaction mixture was stirred at RT for 6 h. Reaction was stopped by the addition of saturated NaHCO$_3$ (30 mL) and ethyl ether (50 mL). The layers were separated and the aqueous layer was extracted with ethyl ether (2×20 mL). The combined organic layers were dried over Na$_2$SO$_4$, filtered, and evaporated to dryness. Benzoate 21 (520 mg) was obtained after silica gel column chromatography (hexane to 15% EtOAc in hexane).

Bis-MOM cyclic product 23. Tetrabutylammonium fluoride ("TBAF", 5 mL, 1.0 M in THF) was added to benzoate 21 (520 mg, 0.628 mmol) at RT. The reaction mixture was stirred at RT for 2 h, then at 40° C. for 15 h. The reaction was stopped by addition of NaHSO$_4$ (300 mg in 30 mL water) and ethyl ether (50 mL). The layers were separated and the aqueous layer was extracted with ethyl ether (2×20 mL). The combined organic layers were dried over Na$_2$SO$_4$, filtered through a pad of silica gel, concentrated, azeotroped with toluene (2×20 mL), dissolved in DCM (20 mL), and dried over 4 A molecular sieves for 2 h. The crude product used for next step without purification.

The above crude product in DCM was added to a refluxing solution of 2-chloro-1-methylpyridinium iodide (460 mg, 1.8 mmol) and diisopropylethylamine in dry DCM (60 mL) over 8 hours. The reaction mixture was refluxed for 18 h. After silica gel column chromatography, 36 mg of cyclic product where the 2-MOM group had been lost ("2-desMOM product") and 114 mg of a mixture of 2-desMOM product plus bis-MOM cyclic product 23 were obtained. The 2-desMOM product was converted to product 23 by dissolving it in DCM, adding DBU (20 eq) and MOMCl (10 eq), and stirring at 35° C. for 5 h. The reaction was quenched by adding ethyl ether (10 mL) and saturated NH$_4$Cl (10 mL). The layers were separated and the aqueous was extracted with ethyl ether (2×20 mL). The combined organic layers were dried over Na$_2$SO$_4$, filtered, and evaporated to dryness. The product was filtered through a pad of silica gel and the solvent was removed with a rotary evaporator. The 114 mg mixture was similarly converted to product 23. The crude product was used for next step without further purification.

Debenzoylated product 25. To a solution of product 23 (33 mg) in EtOH (1 mL) and THF (1 mL) was added NaOH solution (1 mL, 1 N). The reaction mixture was stirred at 37° C. for 16 h and diluted with ether (20 mL) and water (10 mL). The layers were separated and the aqueous layer was extracted with ethyl ether (3×10 mL). The combined organic layers were washed with brine, dried over Na$_2$SO$_4$, filtered, and evaporated to dryness. Debenzoylated product 23 (18.2 mg) was obtained after silica gel column chromatography (10-65% EtOAc in hexane).

Keto lactone 27. To the solution of debenzoylated product 25 in dry DCM (1 mL) was added 4 A molecular sieve and pyridinium chlorochromate ("PCC"). The reaction mixture was stirred at RT for 1 hour, diluted with hexanes (1 mL), filtered through a pad of silica gel and celite, and washed with ether. The solvent was removed and the product keto lactone 27 was used for next step without further purification.

Figure 5:
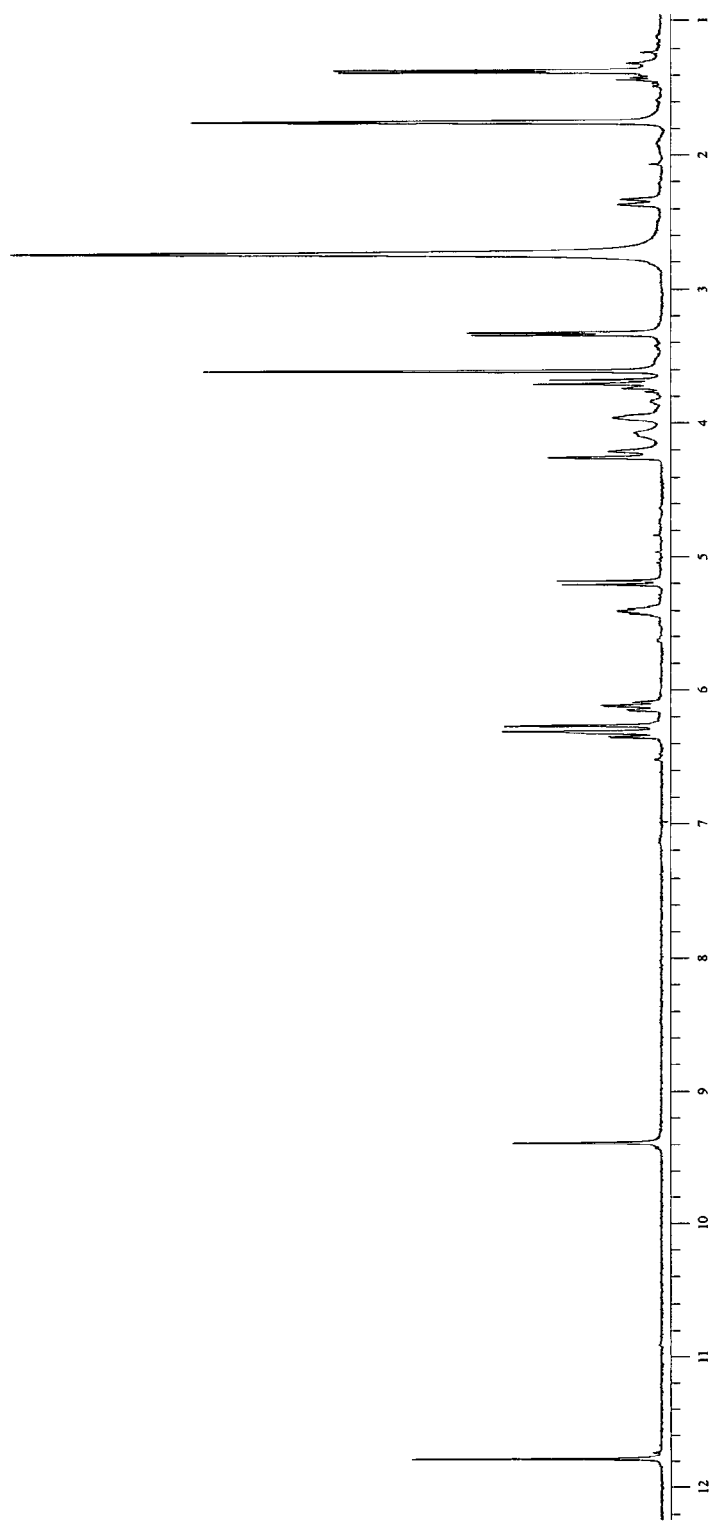
FIGS. 5 and 6 show the $^1$H NMR and $^{13}$C NMR spectra, respectively, of a compound of this invention.
Figure 6:
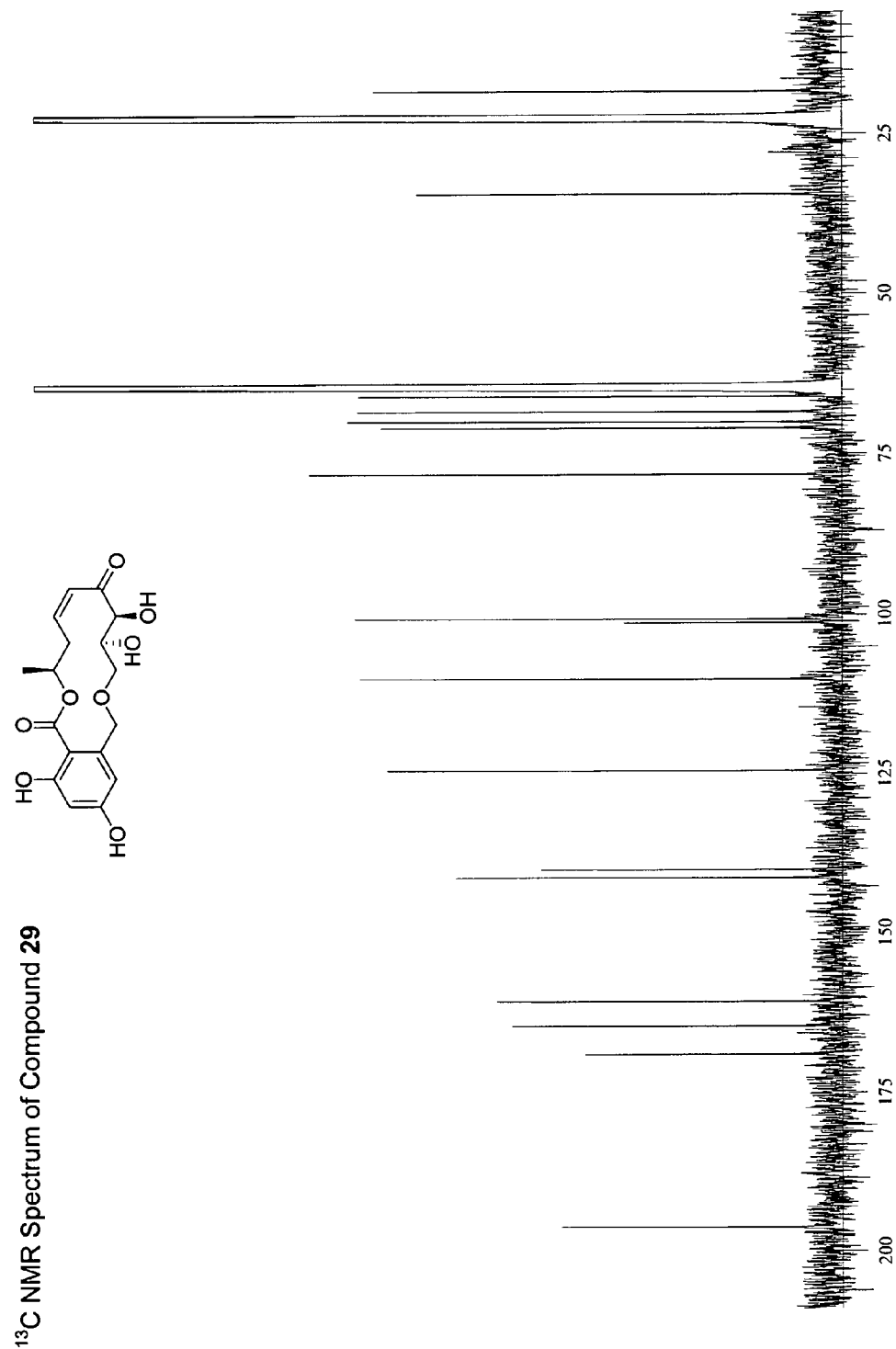

Compound 29. To a solution of keto lactone 27 in acetonitrile (1 mL) was added hydrofluoric acid (0.33 mL). The reaction mixture was stirred at RT for 1 h and quenched by adding to a suspension of $NaHCO_3$ (0.9 g) in THF (10 mL). The mixture was stirred at RT for 10 minutes, filtered through a pad of silica gel, and washed with THF. The solvent was removed and the product (3-4 mg) was purified by silica gel column chromatography (20%-70% THF in hexane). Some very non-polar impurity was removed by filtration through a C18 plug (washed with MeOH). The $^1H$ NMR and $^{13}C$ NMR spectra of RAL analog 29 are shown in FIGS. 5 and 6, respectively. Mass spectrum: $(M+Na^+)=375.1054$; $(M-H^+)=351.1438$.

EXAMPLE 5

Compound 30

This example describes the synthesis of another compound of this invention, namely compound 30. The synthetic scheme also is shown in FIG. 4. The $^1H$ NMR spectra of the products obtained were in each instance consistent with the assigned structures. Further, additional analytical data were obtained for compound 30.

Yne-diol 16. Isopropyl magnesium chloride (4.48 mL, 8.96 mmol, 2.0 M in tetrahydrofuran ("THF") was added to a solution of acetylenic TBS ether 14 (1.9 g, 8.96 mmol) in THF (5 mL) at 0° C. The reaction mixture was heated to 50° C. and stirred at that temperature for 1 hour, cooled to 0° C. A solution of tetrahydrofuran-2-ol 8 (730 mg, 4.56 mmol) in 6 mL THF was added. The reaction mixture was stirred at RT for 2 h, quenched by addition of saturated $NaH_2PO_4$ (35 mL). The aqueous layer was extracted with EtOAc (4×50 mL). The combined organic layers were dried over $Na_2SO_4$, filtered, and evaporated to dryness. Two diastereomers were obtained and used directly in the next step.

Ene-diol 18. Lindlar catalyst (292 mg) and quinoline (15 µL) were added to a solution of yne-diol 16 (1.138 g) in hexanes (56 mL). The reaction mixture was degassed, filled with $H_2$ three times, and stirred under $H_2$ for 2.5 hours. The reaction mixture was filtered through a pad of silica gel and concentrated. Ene-diol 18 (686 mg) was obtained after separation of the two diastereomers by silica gel column chromatography (5% EtOAc/hexane to 35% EtOAc/hexane gradient).

Alcohol 20. Potassium t-butoxide (1.0 M in THF, 0.251 mL) was added dropwise to ene-diol 18 (90 mg, 0.251 mmol, 1 eq) in dimethoxyethane (0.5 mL) at RT. The combination was stirred at RT for 10 min. Benzylic bromide 5 in THF (0.6 mL) was added dropwise. After stirring at RT for 30 min, EtOAc (40 mL) was added. The organic phase washed with water (2×20 mL), dried over $Na_2SO_4$, filtered, and evaporated to dryness. Alcohol 20 (100 mg) was obtained after silica gel column chromatography (hexane to 20% EtOAc/hexane).

Benzoate 22. To a solution of alcohol 20 (700 mg, 0.963 mmol) in dry DCM (10 mL), was added diisopropylethylamine (0.84 mL, 4.815 mmol), benzoic anhydride (435 mg, 1.926 mmol), and 4-dimethylaminopyridine ("DMAP", 118 mg, 0.963 mmol). The reaction mixture was stirred at RT for 6 h. Reaction was stopped by the addition of saturated $NaHCO_3$ (30 mL) and ethyl ether (50 mL). The layers were separated and the aqueous layer was extracted with ethyl ether (2×20 mL). The combined organic layers were dried over $Na_2SO_4$, filtered, and evaporated to dryness. Benzoate 22 (705 mg) was obtained after silica gel column chromatography (hexane to 15% EtOAc in hexane).

Bis-MOM cyclic product 24. Benzoate 22 (~0.360 mmol) was dissolved in THF (5 mL). TBAF (1 M in THF, 3 mL) was added. The reaction mixture was stirred at 50° C. for 5 h. EtOAc (180 mL) was added. The organic phase washed with saturated $NH_4Cl$ (90 mL). The aqueous layer was extracted with EtOAc (2×90 mL). Triethylamine (1.5 mL) was added to the combined organic phases, which were then dried over $Na_2SO_4$, filtered, and evaporated to dryness. The crude product was azeotroped with toluene three times in the presence of triethylamine and used for next step without purification. A solution of the crude product in DCM (60 mL) was added over 2 h to a refluxing solution of 2-chloro-1-methylpyridinium iodide (275 mg) and triethylamine (250 µL) in DCM (60 mL). The reaction mixture was refluxed for 42 h. The solvent was removed and the product (60 mg) was obtained after silica gel column chromatography (5 to 45% EtOAc/hexane gradient).

Debenzoylated product 26. To a solution of product 24 (60 mg) in EtOH (3 mL) and THF (3 mL) was added NaOH solution (3 mL, 1 N). The reaction mixture was stirred at 37° C. for 16 h and diluted with ether (20 mL) and water (10 mL). The layers were separated and the aqueous layer was extracted with ethyl ether (3×10 mL). The combined organic layers were washed with brine, dried over $Na_2SO_4$, filtered, and evaporated to dryness. Debenzoylated product 24 (37 mg) was obtained after silica gel column chromatography (10-65% EtOAc in hexane).

Keto lactone 28. To the solution of debenzoylated product 26 in dry DCM (1 mL) was added 4 A molecular sieve and pyridinium chlorochromate ("PCC"). The reaction mixture was stirred at RT for 4 hours diluted with DCM (100 mL). The organic layer was washed with sat. $NaHCO_3$ (3×100 mL), dried over $Na_2SO_4$, filtered, and evaporated to dryness. The product keto lactone 28 (25 mg) was obtained after silica gel column chromatography (5-45% EtOAc in hexane).

Figure 7:
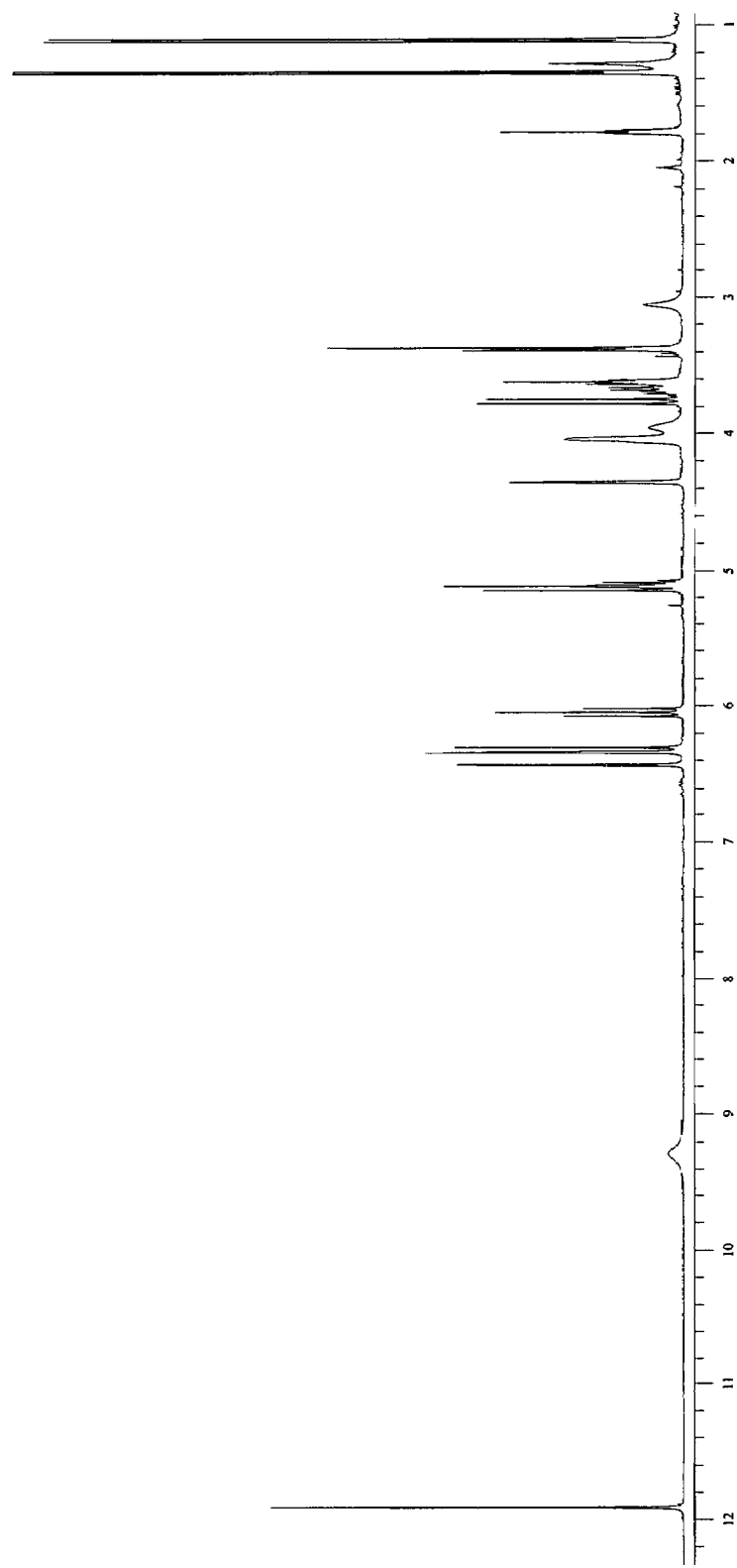
FIGS. 7 and 8 show the $^1$H NMR and $^{13}$C NMR spectra, respectively, of another compound of this invention.
Figure 8:
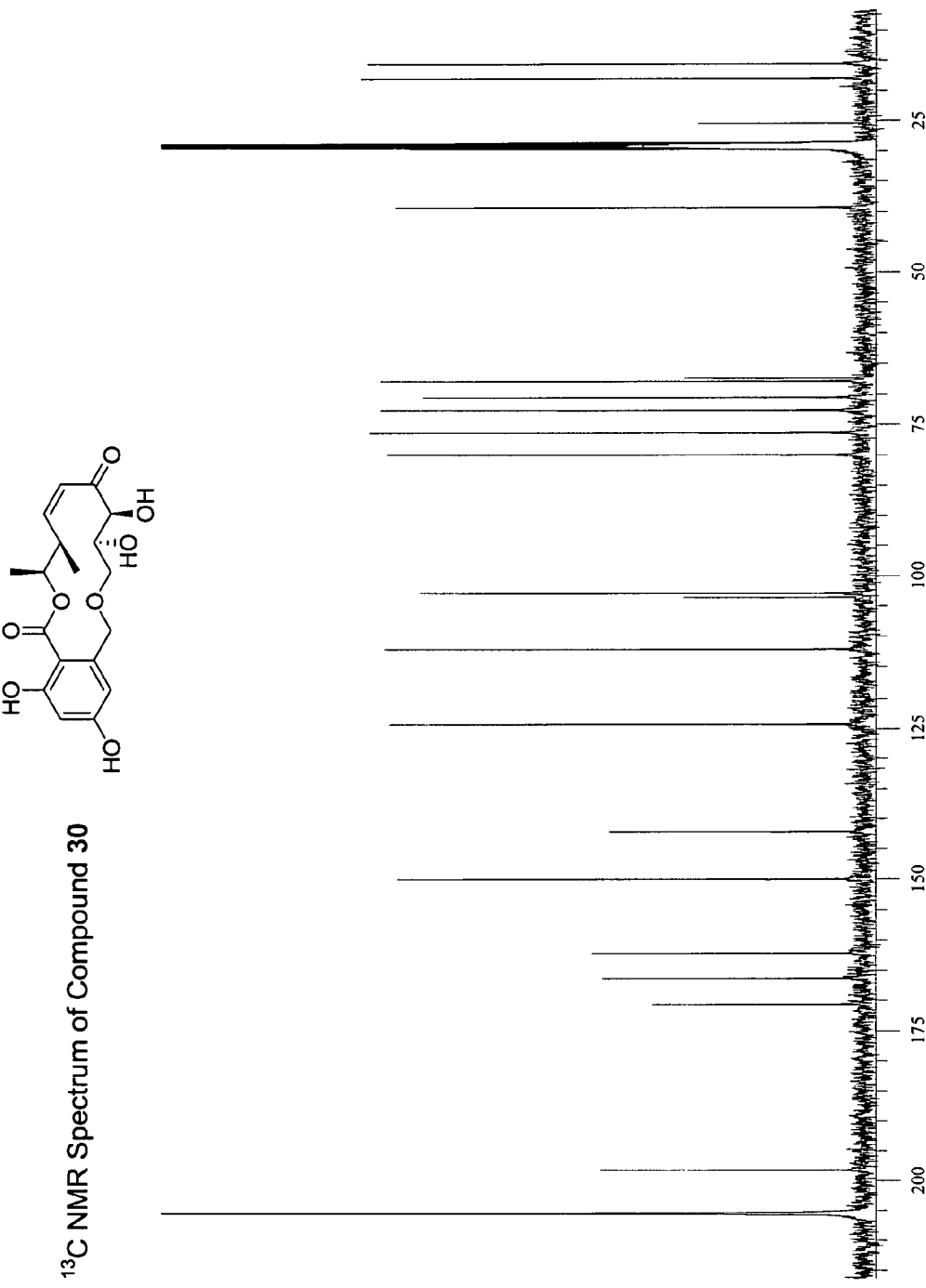

Compound 30. To a solution of keto lactone 28 in acetonitrile (17 mL) was added hydrofluoric acid (4 mL, 48%). The reaction mixture was stirred at RT for 3 hours. Hydrofluoric acid (1 mL, 48%) was added and the reaction was stirred at room temperature for 1 hour. The reaction was poured into DCM (300 mL) and sat. $NaHCO_3$ (100 mL) and the mixture was stirred until no bubbling observed. The layers were separated and the aqueous layer was extracted with DCM (3×200 mL). The combined organic layers were dried over $Na_2SO_4$, filtered, and evaporated to dryness. The residue was then dried under high vacuum overnight. Final product compound 30 (19 mg) was obtained. Its $^1H$ NMR and $^{13}C$ NMR spectra are shown in FIGS. 7 and 8, respectively. Mass spectrum: $(M+H^+)=367.0$.

Those skilled in the art will appreciate that the examples provided above can be adapted, *mutatis mutandis*, to make other compounds of this invention. For instance, compounds of formula I wherein $R^2$ or $R^3$ is H can be used as precursors for the synthesis of compounds of formula I where they are other than H by the application of techniques well known for functionalizing phenolic hydroxyl groups. Particular reference is made to the techniques disclosed in Giese et al., U.S. Pat. No. 5,795,910 (1998); Chiba et al., US 2004/0224493 A1 (2004); and Santi et al., US 2006/0079494 A1 (2006), the disclosures of which are incorporated herein by reference, which can be adapted to the making of compounds of this invention.

EXAMPLE 6

Biological Activity

The biological activity of compounds III and IV is compared against that of the natural product hypothemycin in Table A. Inhibitory concentrations against three cancer cell lines is provided. COLO829 B is a human melanoma cancer cell line having a B-Raf V600E mutation. HT29 is a human colon cancer cell line also having a B-Raf V600E mutation. SKOV3 is a human breast cancer cell line having wild-type B-Raf. Additionally, $K_i$ and $K_{inact}$ for ERK2 are provided.

TABLE A

Biological Activity of Compounds of the Invention

| Activity | Hypothemycin | Compound III | Compound IV |
|---|---|---|---|
| Inhibitory Concentration ($IC_{50}$, μM) | | | |
| COLO829 (B-Raf V600E) | 0.046 | 0.36 | 0.31 |
| HT29 (B-Raf V600E) | 0.26 | 0.86 | 1.42 |
| SKOV3 (wild-type B-Raf) | 4 | 74 | >100 |
| ERK2 Binding | | | |
| $K_i$ (μM) | 2.7 ± 0.8 | 3.1 ± 0.4 | — |
| $K_{inact}$ (sec$^{-1}$) | 5 ± 2 × 10$^{-3}$ | 0.91 ± 0.4 × 10$^{-4}$ | — |

The $IC_{50}$ data show that compounds III and IV of this invention are especially effective as inhibitors of cancer cells having a BRaf V600E mutation.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

What is claimed is:

1. A compound having a structure represented by formula I

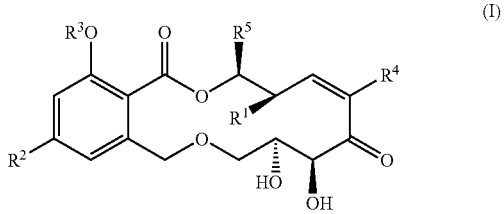

and the pharmaceutically acceptable salts thereof, wherein
$R^1$ is H or $C_1$-$C_4$ alkyl;
$R^2$ is H, hydroxyl or protected hydroxyl;
$R^3$ is H or $C_1$-$C_4$ alkyl;
$R^4$ is H; and
$R^5$ is H or $C_1$-$C_4$ alkyl.

2. A compound according to claim 1, having a structure represented by formula (II)

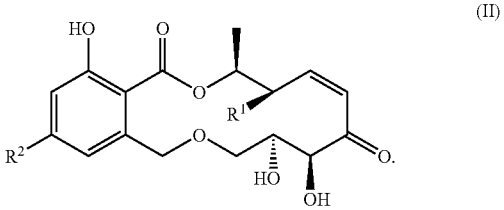

3. A compound according to claim 2, wherein $R^1$ is H or $C_1$-$C_4$ alkyl and $R^2$ is OH or protected hydroxyl.

4. A compound according to claim 3, wherein $R^1$ is H or $CH_3$.

5. A compound according to claim 1, having a structure represented by formula III:

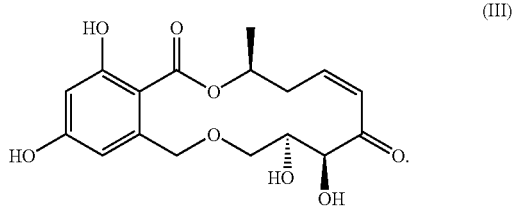

6. A compound according to claim 1, having a structure represented by formula IV:

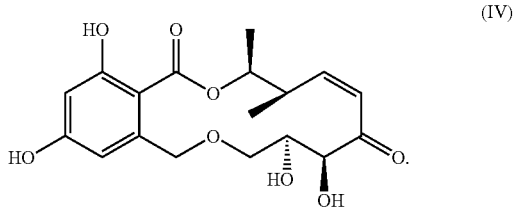

* * * * *